United States Patent
McGeehan

(10) Patent No.: US 8,449,285 B2
(45) Date of Patent: May 28, 2013

(54) SYSTEMS AND METHODS FOR MICRO-CONTACT STAMPING

(75) Inventor: John K. McGeehan, McDaniel, MD (US)

(73) Assignee: Hepregen Corporation, Medford, MA (US)

( * ) Notice: Subject to any disclaimer, the term of this patent is extended or adjusted under 35 U.S.C. 154(b) by 371 days.

(21) Appl. No.: 13/011,734

(22) Filed: Jan. 21, 2011

(65) Prior Publication Data

US 2012/0187082 A1    Jul. 26, 2012

(51) Int. Cl.
*C23F 1/00*    (2006.01)
*B29C 59/02*    (2006.01)

(52) U.S. Cl.
USPC ......... 425/385; 425/440; 425/387.1; 264/2.5; 264/219; 264/293

(58) Field of Classification Search
USPC .................. 264/219, 2.5, 293; 425/385, 470, 425/403, 387.1, 440
See application file for complete search history.

(56) References Cited

U.S. PATENT DOCUMENTS

| | | | | |
|---|---|---|---|---|
| 7,635,262 B2 * | 12/2009 | Chou et al. | ..................... | 425/385 |
| 7,645,133 B2 * | 1/2010 | Jeong et al. | ..................... | 425/385 |
| 7,845,928 B2 * | 12/2010 | Finkowski et al. | ........... | 425/299 |
| 7,931,844 B2 * | 4/2011 | Lof | ................. | 264/293 |
| 8,087,920 B2 * | 1/2012 | Cho et al. | ....................... | 425/150 |
| 2002/0186649 A1 * | 12/2002 | Feist et al. | .................... | 369/280 |
| 2003/0025227 A1 * | 2/2003 | Daniell | ........................... | 264/2.5 |
| 2003/0159608 A1 * | 8/2003 | Heidari | ........................... | 101/494 |
| 2005/0178280 A1 * | 8/2005 | Lee et al. | ....................... | 101/453 |
| 2006/0246169 A1 * | 11/2006 | Chen et al. | ..................... | 425/385 |
| 2007/0195718 A1 * | 8/2007 | Lee et al. | ....................... | 370/260 |
| 2011/0216412 A1 * | 9/2011 | Reed et al. | ..................... | 359/530 |

FOREIGN PATENT DOCUMENTS

| | | |
|---|---|---|
| DE | 3218857 A1 | 11/1983 |
| EP | 1323465 A1 | 7/2003 |

OTHER PUBLICATIONS

Thibault et al "Direct Micro-contact priting of Oligonucleotides for Biochip applications," Journal of Neurobio Technology, 2005, 3:7, Jul. 1, 2005.
International Search Report and Written Opinion dated May 16, 2012 in International Application No. PCT/US2012/021214.

* cited by examiner

*Primary Examiner* — Joseph S Del Sole
*Assistant Examiner* — Nahida Sultana
(74) *Attorney, Agent, or Firm* — Ropes & Gray LLP

(57) ABSTRACT

Systems and methods for using stamps to print or mask materials on a substrate service. In one particular embodiment, the systems and methods include a microcontacting stamp that has a plurality of rigid posts each having a resilient pad at its distal end. Each post is fitted within an aperture located in a guide plate such that the post may move longitudinally within the guide plate. The guide plate includes a variety of apertures that typically are aligned with the wells of a microtiter plate. The apertures extend typically through the entire thickness of the guide plate. On one side of the guide plate is a resilient member that extends over one or more of the apertures thereby holding the post in place.

20 Claims, 8 Drawing Sheets

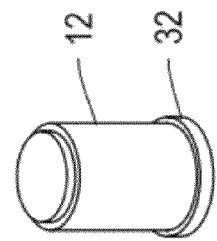
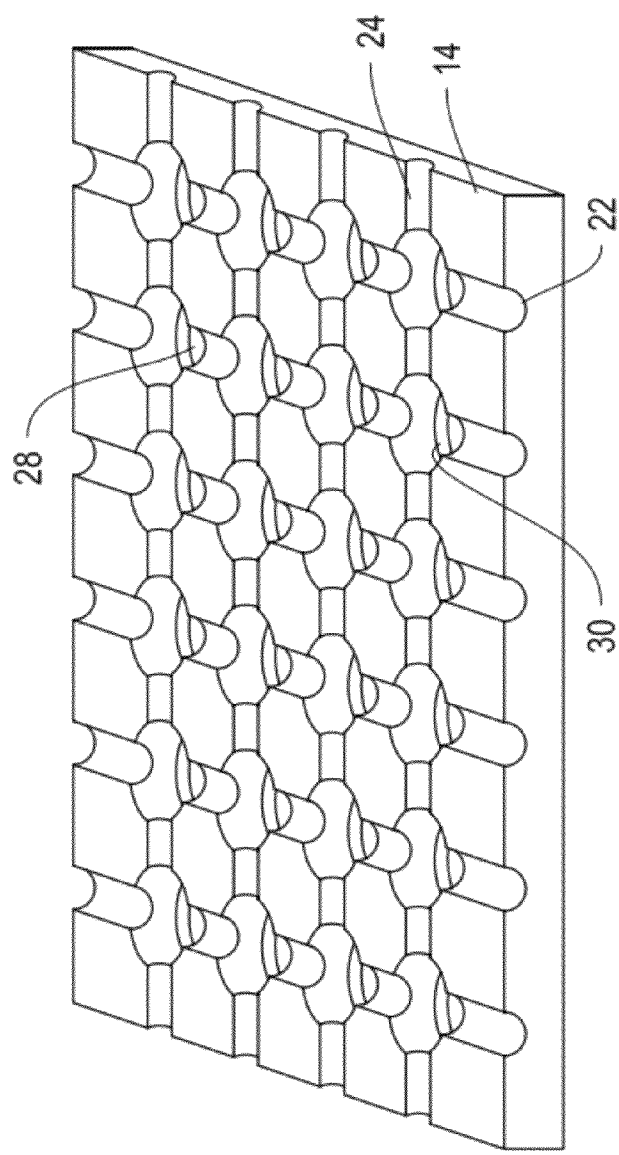
Fig. 3B
Fig. 3A

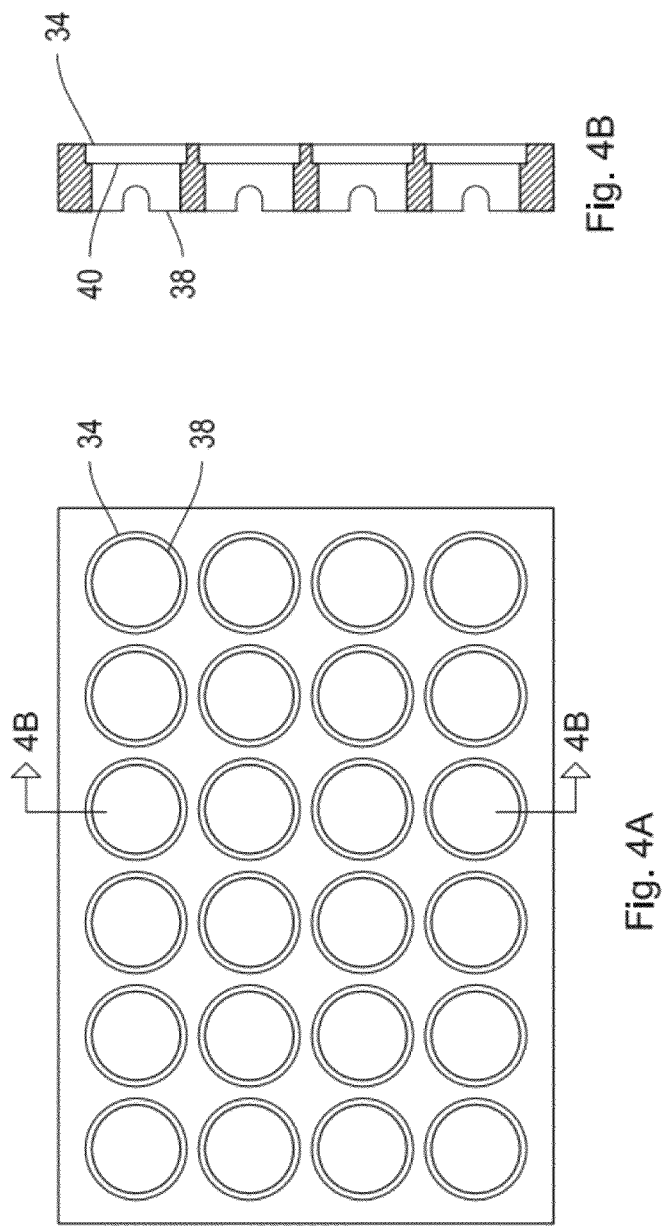
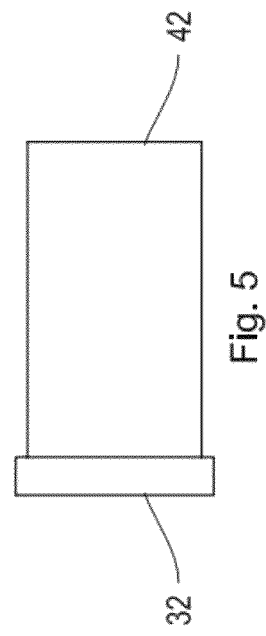

PLATE PATTERNING ISSUES - "DONUT EFFECT"

UN-ETCHED SURFACE DUE TO OVERCOMPRESSION

HEPATOCYTE ISLAND

CLEAN ETCHED SURFACE FOR FIBROBLAST ATTACHMENT

SYSTEMS AND METHODS FOR MICRO-CONTACT STAMPING

FIELD OF THE INVENTION

The systems and methods described herein relate to methods and systems for forming patterns of cells on a substrate surface.

BACKGROUND

Custom cell culture environments offer great promise. Cell cultures and cell co-cultures may allow scientists to discover cell behavior and to safely determine whether a proposed therapeutic agent may be effective as well as safe for treating a particular disease. Recent advances in micropattern cell culture development have proven invaluable in increasing our understanding of the structure-function relationships of multi-cellular communities. Such micropattern cell cultures yield more control over cell-cell interaction, particularly when precise and reliable cell spacing is achieved. The study of tissue organization at the micro-environment level has revealed insights into areas as diverse as angiogenesis, hepatocyte function, calcification of bone derived cells and neuronal growth cone guidance. Additionally, micropattern cell cultures provide researchers with the ability to scale their experiments and thereby more effectively and efficiently conduct tests and experiments in parallel. This increases the rate at which scientific discovery can occur and speeds the development of new drugs and more quickly elucidates the mechanisms of certain diseases.

However, forming micron level cellular islands can be a difficult process as it requires tools that can precisely manipulate small quantities of cells, such that cells are spaced close enough to be measured in microns. Additionally, cells and other biological material that are needed to build the cellular islands are delicate and readily perishable, thereby requiring manipulation techniques that are not caustic, or otherwise harmful to the biological materials being manipulated.

Numerous techniques have been investigated for forming cellular islands on a substrate. These techniques include the chemical modification by photolithography of a glass substrate, and jet printing techniques that use small, low temperature printing heads to dispense drops of liquid that carry cellular material to the substrate. One such printing technology includes the Celljet cell printer manufactured and sold by the Digilab Company of Holliston, Mass. The Celljet printer prints cells as part of a liquid dispensing operation that dispenses a droplet of fluid containing cells. The droplet may be dispensed onto a microtiter plate or to a multi-plate. Other techniques for forming cellular islands include micro-contact printing and laser directed cell writing. Direct micro-contact printing typically involves the use of a structured, inexpensive, elastomeric stamps usually made of polydimethylsiloxane (PDMS) which have a relief pattern at the micron scale. These stamps usually allow the parallel deposition of molecules onto the target substrate surface. During contact, materials from the PDMS stamp are transferred onto the substrate. This transfer requires an efficient and usually quick transfer of molecules from the stamp surface to the substrate. One such technique is described in Direct Micro-contact Printing of Oligonucleotides for Biochip Applications, Thibault, et al. Journal of Neurobio Technology (2005) 3:7. As described in this reference, an electrobeam lithography approach, was used to etch a silicone master mold into which liquid PDMS may be poured. The liquid PDMS may be degassed, and then cured thermally. The PDMS may then be removed from the master to provide a stamp which can be used multiple times, depending upon the surface chemistries. The micron features of the stamp contact a substrate and prints a material onto the substrate at the point of contact. The success of the process depends in part on the successful contact of the elastomeric stamp with the substrate.

The physical contact between the micron features of the elastomeric stamp and the substrate must be made precisely and consistently across the stamp or the elastomeric material will fail to act as a proper mask during the etch process or fail to print the desired material onto the substrate. Sometimes it is the case that only partial contact is made and a result is a "coffee ring" pattern that correctly forms a perimeter of the pattern but fails to make successful contact for the interior portion of that pattern. Failure to form correct patterns means that the testing or experiment protocol cannot be followed and this can prevent the patterned substrate from being used within the experiments.

Accordingly, there is a need in the art for systems and methods that provide improved micro-contact stamps and stamp processes.

SUMMARY OF THE INVENTION

The systems and methods described herein include, inter alia, a microcontacting stamp that may be employed as a patterning stamp to form patterns of cells on the bottom floor of the wells of a microtiter plate. The microcontacting stamps described herein provide improved well-to-well and plate-to-plate reproducibility and provide a set of stamping posts that can individually move relative to each other to achieve more consistent contact with a substrate surface and thereby produce precisely formed cell patterns with improved repeatability and reliability. In other aspects, the systems and methods described herein include methods for forming patterns of cells by printing or masking and methods for manufacturing stamps for forming pattern of cells. However, it will be understood that the systems and methods described herein can be adapted and modified for other suitable applications and that these additions and modifications do not depart from the scope hereof.

In certain embodiments, the systems include devices for forming patterns of cells on a surface of a substrate. The devices may have a guide plate having an upper surface and a lower surface and a plurality of apertures extending through the plate and being arranged to align with locations on the surface of the substrate, a plurality of posts fitted within respective apertures, a plurality of pads formed of a resilient material and having a pattern of raised plateaus for butting against the surface the substrate, each of the plurality of pads being fixed to a distal surface of a respective post, and a resilient deformable linkage connecting the posts within the guide plate.

Optionally, the device may also include a clamp plate disposed above the guide plate upper surface for applying a mechanical load across the upper surface of the guide plate. A clamp may force the clamp plate against the guide plate with a force selected to seal the pads against the surface of substrate.

In some embodiments, the resilient deformable linkage includes a section of resiliently deformable material. The resilient deformable linkage may be a foam pad disposed above and optionally adhered to the upper surface of the guide plate, and the ILD of at least a portion of the linkage, such as for example the first five thousands of an inch of the foam pad, is less than the force required to deform the pattern of the pad on the distal end of a post. Although the linkage may be a foam pad, foam buttons fitted into the apertures, air bladders fitted within the apertures, springs and other mechanical elements, or any other suitable mechanism may be employed.

Typically, although not always, the pads include a resilient mask for butting against a surface of the substrate. The pad may be a print pad for delivering a biological material to the surface of the substrate, and the pad may be a mask that masks a portion of the surface during an etch or wash process.

Optionally, the guide plate includes gas channels in fluid communication with the apertures for delivering plasma gas into the apertures. The guide plate apertures may be arranged to dispose the plurality of posts in alignment with the wells of a multi-well microtiter plate. The posts may comprise rigid acrylic posts and the pads may comprise PDMS.

In some embodiments, the posts have a retaining member for preventing the posts from passing through the apertures.

In another aspect, the invention provides manufacturing methods, including manufacturing methods for making a patterning mask of the type that forms a pattern of cells onto a surface. These methods may include the steps of providing a mask having a desired pattern and being made of a material having some resilience to a mechanical force, attaching the mask at one end of a post, inserting the post within a guide plate such that the post is movably disposed within the guide plate to allow linear movement of the post, and providing a compressible layer over the guide plate and into contact with the post, such that the post is held within the guide plate by the compressible layer.

In some practices, the methods include selecting a compressible layer having an indentation load defection ILD selected to resiliently yield at a force less than the force required to deform the mask. Optionally, a plurality of gas channels may be formed in fluid communication with the apertures for delivering plasma gas into the apertures. The posts may be formed as rigid cylindrical members having a diameter selected to fit within a well of a microtiter plate.

In a further aspect, the invention provides methods for forming patterns of cells within the wells of a microtiter plate, such as methods that provide a microcontacting stamp having a guide plate with an upper surface and a lower surface and a plurality of apertures extending therethrough and arranged to align with the wells of the microtiter plate, a plurality of posts fitted within respective apertures and having resilient pads on their distal ends, the pads having raised plateaus for forming the pattern of cells, and a resilient deformable linkage connecting the posts within the guide plate, fit the microcontacting stamp within the microtiter well, and apply a clamping force to drive the microcontacting stamp against the microtiter plate to press the pads against the bottom surface of the wells of the microtiter plates.

In such methods, one may apply cells to the resilient pads and press the pads against the bottom surface of the wells to print the cells on to the surface of the well. In alternative practices, one may apply a cell adhering material to the bottom surface of the microtiter wells, form in the guide plate, gas channels that are in fluid communication with the apertures, and deliver plasma gas through the gas channels and into the apertures, to etch the cell adhering material from the surface of the microtiter well.

Other applications and modifications of the invention will, in part, be obvious, and, in part, be shown from the following description of the systems and methods shown herein.

BRIEF DESCRIPTION OF THE DRAWINGS

The foregoing and other objects and advantages of the invention will be appreciated more fully from the following further description thereof, with reference to the accompanying drawings wherein;

FIG. 3A-3B depict certain separate components of the micro-contact stamp depicted in FIG. 1;

FIGS. 4A-4B depict a schematic view of one guide plate;

FIG. 5 depicts a schematic view of one post according to the invention;

DESCRIPTION OF THE ILLUSTRATED EMBODIMENTS

Figure 1:
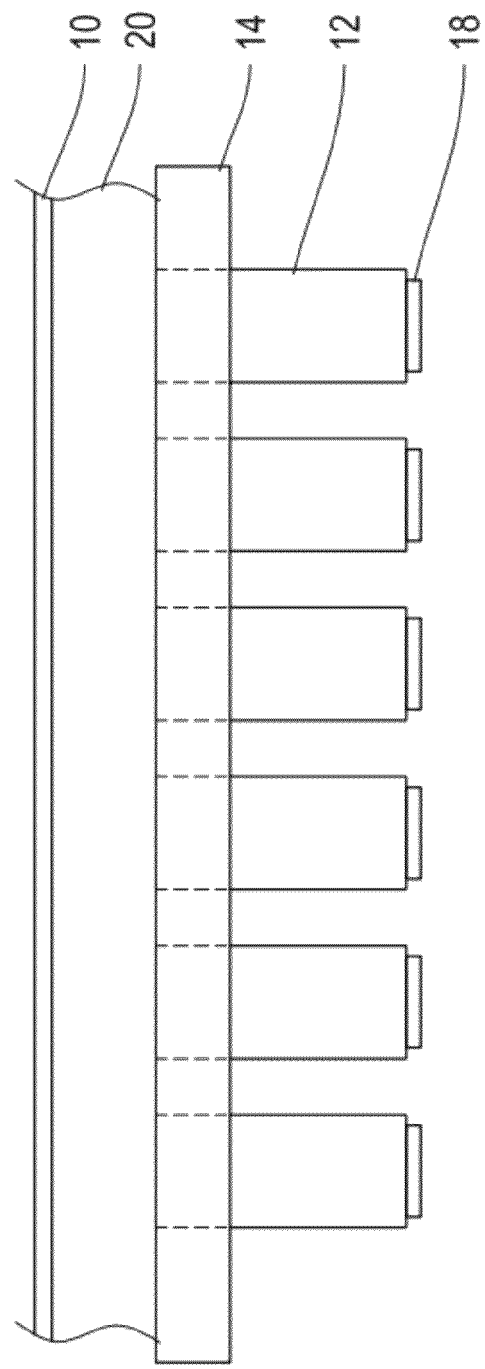
FIG. 1 depicts one embodiment of a micro-contact stamp according to the invention.

To provide an overall understanding of the invention, certain illustrative embodiments will now be described, including a microcontacting stamp system that can be employed as a patterning stamp to form patterns on the bottom floor of the wells of a microtiter plate used to provide improved well-to-well and plate-to-plate reproducibility. In an embodiment, the micro-contacting stamp provides a set of stamping posts that can individually move relative to each other to provide more consistent contact with a substrate surface and thereby produce precisely formed cell patterns with improved repeatability and reliability. However, it will be understood by one of ordinary skill in the art that the systems and methods described herein can be adapted and modified for other suitable applications and that such other additions and modifications will not depart from the scope hereof.

As will be described herein, the micro-contacting stamp may be used as a pattern mask that covers and protects a coated surface during an etching process to thereby leave a pattern of coating on the surface. In a subsequent step, cells may be washed over the pattern so that the cells adhere to the coating and form islands of cells in the pattern left by the etching process. Alternatively, the micro-contacting stamp may be used to print cells or other material directly onto a substrate surface, such as a slide, the bottom walls of a multi-well microtiter plate or a multi-plate. Still other uses and applications may be addressed by the systems and methods described herein.

In one embodiment, a micro-contacting stamp has a guide plate with a plurality of apertures. Posts slide into each of the apertures, and the posts have a lip at one end that is larger than the aperture and keeps the post from sliding completely through. A resilient member fits over the guide plate and covers the posts so that the posts are held within the apertures.

In use, the micro-contacting stamp may be aligned above and fit into a microtiter plate, such that each post fits within a respective well of the microtiter plate. A force applied to the guide plate and directed downward toward the bottom surface of the microtiter plate brings the resilient pads at the respective ends of the posts into contact with the bottom surfaces of the respective wells of the microtiter plates. As each post contacts the bottom surface of the microtiter well, the force that will be applied against the bottom surface of the micro-titer well is regulated in part by the resilient character of the resilient member placed above the apertures. In one embodiment the resilient member is a layer of open cell polyurethane foam. The resilient characteristic of this foam pad may be associated with the indentation load deflection (ILD) characteristic of the open cell foam pad. Thus, the force with which the post will press against the bottom surface of the microtiter well is regulated by the ILD of the foam pad resilient member holding that post within the aperture of the guide plate.

FIG. 1 depicts one embodiment of a micro-contact stamp 10. Specifically, FIG. 1 depicts a micro-contact stamp 10 having a plurality of post 12 each having a respective resilient pad 18 located on a distal end of post 12. Each post is fitted within an aperture (not shown) within a guide plate 14. Above the guide plate is a resilient number 20, which in FIG. 1 is depicted as a pad of material, such as open cell foam material, latex material or some other resilient material.

Figure 2A:
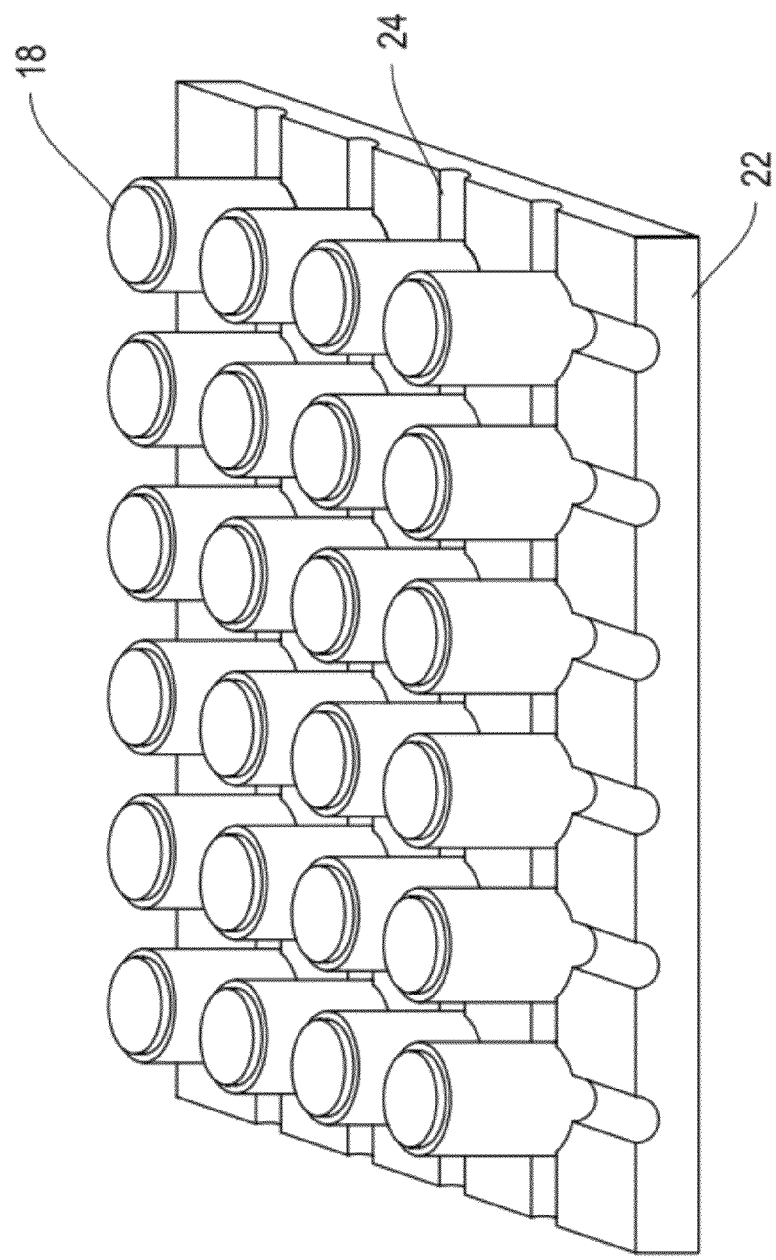
FIG. 2A depicts the stamp of FIG. 1 from a different perspective.

The depicted posts 12 are typically formed of a rigid material and are typically made from acrylic, however any suitable material may be employed. In the embodiment shown in FIG. 1 there are a plurality of posts 12 each of which fits through an aperture in the guide plate 14 and extends downwardly from the guide plate 14. FIG. 2 depicts the microcontacting stamp 10 of FIG. 1 from a different perspective. Specifically, FIG. 2A shows the posts 12 as pointing upwardly and presents a bottom up view of the microcontacting stamp 10. FIG. 2A illustrates that the posts 12 are seated within the guide plate 14 and aligned in a matrix of rows and columns. The rows and columns shown in FIG. 2A are selected to align with the wells of a corresponding microtiter plate such that each post 12 will fit within a respective one of the wells of a microtiter plate. Leg post 12 is cylindrical as shown in FIG. 2 and the geometry and width of the post 12 is selected such that the post 12 fits within, although preferably fits snugly within, the corresponding well of the microtiter plate. As further shown in FIG. 2A, each of the resilient pads 18 is centered on the distal end of a respective post 12. Each resilient pad 18 is circular in shape and has a thickness of approximately 2-3 millimeters. The resilient pad 18 has a smaller diameter than the diameter of the leg post 12. The particular diameter of the resilient pad 18 will be selected according to the criteria of the application, as the diameter of the resilient pad 18 will relate to the number of cellular islands formed on the bottom of each microtiter well. Additionally, the smaller diameter of the resilient pad 18 will allow, in some embodiments, for a ring to be formed around the periphery of the cellular island wherein that ring may provide spacing from the cells and the side walls from the microtiter plate and may optionally include a peripheral ring that can carry other materials such as fibroblast, growth medium, or some other material that the cells within the islands may draw upon. FIG. 2A further depicts that the guide plate 14 includes a plurality of etch gas row channels 22 and etch gas column channels 24. In this particular embodiment, the microcontacting stamp is to be employed as a mask that will press the elastomeric resilient pads 18 against the surface of the microtiter plate for the purpose of covering a material on the plate during an etching process and thereby protecting that material from the etchart, typically an etching gas. The etching gas may be introduced, at least in part, through the channels 22 and 24. These channels will allow gas to flow across the surface of the guide plate 14 and down into the microtiter plates, etching the portion of the bottom surface of the microtiter plate which is not covered by the resilient pad 18. The stamp 10 depicted in FIG. 2A has twenty four posts and is therefore designed for use with a twenty four well plate. However, in other embodiments the stamp may have posts for a 96 well, 384 well, 612 well or any size micro titer plate. Also, in other embodiments, the posts may be of alternative geometries to match the share of alternate well shafts, or for use with slides or glass or styreve plates that do not have wells.

The resilient pads 18 typically are an elastomer, commonly PDMS. In one embodiment, the PDMS resilient pads are made by a casting process that fabricates the PDMS pads 18 as stamps that will act as the masks during an etching process. In one particular embodiment the PDMS resilient pads 18 are made from PDMS-sylgard 184 silicone elastomer kit. The elastomer is poured into a mold and degassed by vacuum within the mold and then allowing the PDMS to cure in place. After curing, the PDMS micropatterned sheet can be removed from the mold and the individual buttons can be punched out. Alternatively individual buttons can be cast and/or removed individually. The stamp may then be applied to the distal end of the post 12 and the molds are cleaned to remove all non-cured PDMS and materials left behind so that the molds may be used again to form new resilient pads 18.

Figure 2B:
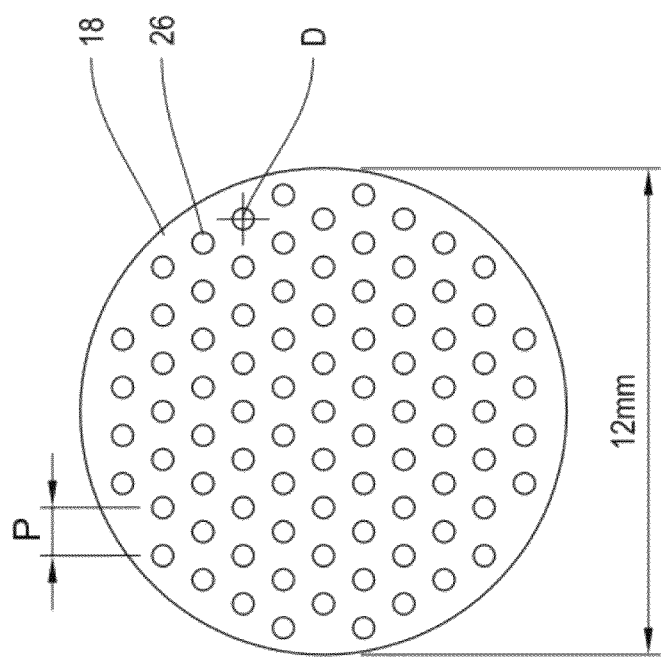
FIG. 2B depicts an enlarged view of the pads of the stamp of FIG. 1.

One particular process for forming the pads 18 will now be described. In this process, the pads 18 are formed as elastomeric discs having a diameter of about 12 mm and may have a durometer Shore-A scale of about 48, however any suitable hardness may be used and the actual hardness selected will depend, at least in part on the application, such as whether the pads are being used as a mask or a printing stamp. On the pads 18 is formed a pattern of spaced plateaus. In one particular example, each plateau is about 500 microns in width, about 100 microns high, and the pitch between plateaus is about 1200 microns. One such pad 18 is depicted in FIG. 2B, which shows a close up magnified view of one of the pads 18 on the end of a post 12 shown in FIG. 2A. Specifically, FIG. 2B shows the face of pad 18 as having a pattern of plateaus 26, each plateaus 26 being about 500 microns in diameter (D) and the pitch (P) between individual plateaus 26 being about 1200 microns. Theses spacings and dimensions are for purposes of example and illustration only and are not to be deemed limiting in anyway. The plateaus 26, in use, will contact the bottom surface of a microtiter plate well and cover a collagen layer, or other biological or chemical substance or other treatment that allows cells to be adhered to the surface that has been applied to the bottom floor of the well. One example process for forming a pad using a silicon wafer master mold having lithographically etched features, is presented below.

Example Process for PDMS casting of a well stamp using a Silicon wafer master mold.

Materials:

PDMS-Sylgard 184 Silicone Elastomer Kit; Net: 0.5 kg; Teflon 96 and 24 well molds, Aluminum foil, plastic corregate, 6×6" glass plates, 6×6" macor ceramic with bored holes, 1/16" thick 6×6" silicone rubber, toluene 70% EToH.

Method:

All mold parts were carefully cleaned after earlier castings by sonicating is about 1 inch of toluene in a B1500A-MTH VWR sonicator for several cycles of 20 minutes each cycle. After sanitizing all mold parts, screws included, any remaining PDMS was scraped or brushed off. Compressed nitrogen was used to blow any remaining PDMS particles out of the threaded holes in the mold. All PDMS is removed. A final rinse with sonification and clean toluene, and then a wiping dry finishes cleaning All parts are then dried for several hours at 100° C. in a Yamoto ADP-31 vacuum or under a partial vacuum to remove vapors.

The Silicon wafer master mold was assembled into a mold assembly that could receive and cure liquid PDMS. The mold was placed on a level surface and checked for level accuracy. A glass plate and a ceramic plate are assembled and clamped, to form a mold into which PDMS may be poured. PDMS polymer was mixed in a 10:1 ratio with the provided initiator. The mixture was centrifuged for 5 minutes to remove air that was introduced during mixing. The PDMS was then poured into the mold and vacuum degassed in repetitive cycles. Cycles were repeated until visual inspection indicated all air/gas trapped in the features of the silicon master mold were removed. After degassing, the castings were allowed to set overnight at room temperature. After overnight curing, the castings were transferred to a 60° C. oven for several hours of additional curing. The mold then was allowed to cool to room temperature, and the now formed and cured PDMS stamp was removed from the mold, with care.

In one embodiment, the mold was prepared from a 100 mm diameter silicon wafer. The wafer was provided with a dense array of etched, circular wells covering most of the wafer surface. Wafer thickness, in one example, was about 0.4-0.6 mm. The circular wells were about 500 microns in diameter, with a uniform spacing of 1200 microns between circle centers in a hexagonal close-pack pattern, and etched to a depth of 100 microns. Silicon on insulator wafers were used in one embodiment to achieve depth tolerances of 1.0 micron within the wafer. A buried oxide layer at the bottom of the wafer provided a hard stop for the silicon etch process. The buried oxide layer can be removed to leave a smooth silicon surface.

From FIGS. 1 and 2A, one can see that the PDMS stamps can be removed from the mold and attached to the distal ends of the posts 12. In the depicted embodiments, the PDMS stamp is a cylindrical button of about 0.3 cm in height and about 1 cm in diameter. The exposed surface of the PDMS stamp, as shown in FIG. 2B, includes a plurality of spaced plateaus that will contact the substrate and separate the rest of the PDMS from the substrate surface.

Returning to FIG. 1, the resilient member 20 is shown from a side view perspective. The depicted resilient member 20 is a foam pad positioned above the floating posts 12. In one embodiment, the pad is an adhesive backed, super resilient one half-inch thick pad manufactured by McMaster-Carr part number 86235K172. In the depicted embodiment, the resilient member 20 covers the entire upper surface of the guide block 14. The resilient member 20 holds the posts 12 within the guide block 14 so that the posts cannot fall out of the block, and in fact are restrained from moving axially more than a fraction of a centimeter. As will be described with reference to FIG. 7, the load deflection and the channel resilience properties of the resilient member allow each post 12 to move axially and somewhat "float" within the aperture. This allows the PDMS plateaus to more reliably make correct physical contact with the bottom surface of the microtiter well.

Alternative embodiments may include resilient foam plugs that fit within the apertures and sit above the posts and beneath a solid plate. In this alternate embodiment the resilient plug is sandwiched between the post 12 and the plate covering the guide plate. This allows the post 12 to push against the resilient foam plug and thereby apply a resisting force that will drive the post 12 downward toward the surface of any substrate below the stamp. In this embodiment, the resilient force applied by the foam plug is selected to be less than the force required to deform the pad 18 as the pad 18 is pressed against the substrate surface, thereby, although not to be bound by theory, reducing the distortion of the pattern formed on the substrate surface.

FIGS. 3A and 3B depict the guide plate 14 and the post 12 as separate elements. FIG. 3A shows the guide plate 14 as a rectangular plastic plate having the plurality of evenly spaced apertures 28. In the depicted embodiment, the guide plate 14 has 24 apertures 28, each of which is aligned with the well of a respective twenty-four well microtiter plate. The depicted guide plate 14 has a thickness selected to reduce lateral movement or shifting of the post 12 as it moves axially within the guide plate 14. As such, the posts 12 are guided by guide plate 14 along an axial path that is orthogonal to the bottom wall of the microtiter plate. The post 12 carries the paid 18 at its distal end and the exposed surface of the pad 18 is substantially parallel to the bottom surface of the microtiter well. Thus, the guide plate 14 guides the posts 12 axially up and down and brings the exposed surface of the pad 18 into parallel contact with the bottom surface of the microtiter plate, or any substrate surface being treated with the microcontacting stamp. As further shown in FIG. 3A the channels 22 and 24 extend as rows and columns through the underside of the guide plate 14. Each aperture 28 depicted in FIG. 3A has a plurality of channel edges 30. Each channel edge 30 allows gas traveling through channels 22 or 24 to travel into the aperture and eventually down into the well of the microtiter plate. In the embodiment depicted in FIG. 3A each aperture 28 has four channel edges 30 such that the channel edges provide fluid communication across the different apertures so that gas flowing under the plate can travel into each aperture 28 and into each well of the microtiter plate.

FIG. 3B depicts the single post 12. The post 12 is a cylindrical body that has a lip 32 which has a larger diameter than the main body of the post 12. In one embodiment the post 12 is made of acrylic and cylindrical in shape, however the material employed and the size and geometry of the post will depend on the application at hand and those of skill in the art can vary the size and geometry of the post as appropriate for the application.

FIGS. 4A and 4B provide a schematic view from different perspective of the guide plate 14. FIG. 4A provides a bird's-eye view of guide plate 14 and shows the twenty-four apertures that are selectively and evenly spaced across the surface of the guide plate 14. In the embodiment depicted in FIG. 4A, the guide plate is approximately 13 centimeters in length and 9 centimeters in width. Each aperture is approximately 1.5 centimeters in diameter. FIG. 4B presents a cutaway side view of the guide plate 14. FIG. 4B shows that the apertures 28 that extend through guide plate 14 have a first portion 34 that is of a larger diameter than the lower portion 38 the upper portion 34 provides a shelf 40 that will butt against a corresponding shelf on the post 14. FIG. 4B further depicts the channel edges 30 that provide fluid communication from the exterior of the guide plate 14 into the interior of the guide plate 14 and into the separate apertures 28.

FIG. 5 illustrates schematically a cross sectional side view of a post 12. In particular, FIG. 5 shows a post 12 that includes a post lip 32 of larger diameter than the post body 42. The post in FIG. 5 is approximately 1.18 centimeters in length and approximately 0.6 centimeters in diameter for the post body 42 and approximately 6.5 centimeters in diameter for the larger post lip 32. The bottom edge of post lip 32 will butt against the shelf 40 in acrylic guide plate 14 shown in FIG. 4B thereby preventing the post 12 from passing through the aperture 28 in the illustrated guide plate in the illustrated guide plate 14.

The post body 42 in the depicted embodiment slides into the aperture 28 and fits therein such that an "air gap" exists between the post body 42 and the side wall 38 of the aperture 28. The size of this gap may vary according to the application, but typically the gap is sufficiently large to allow the etching gas passing through channels 22 and 24 to pass over channel edges 30 and pass through the gap to the bottom wall of the microtiter plate. The gap size is about 1.5 mm, and may be lower to 0.5 mm depending upon the application. One may pull a vacuum to withdraw any air surrounding the posts, then apply O₂ that will draw into the gaps between the posts that are contacting the substrate surface and the O₂ will be ionized by the plasma to create ions for the etching process to take place. As discussed above with reference to FIG. 2A, the resilient pad 18 on the distal end of post 12 has a diameter smaller than the diameter of the post body 42 and the diameter of the microtiter well (not shown). This provides a peripheral ring around the resilient pad that can receive gas. In one practice, the gas is an etching gas, used to etch a material laid on a glass or polystyrene substrate surface.

In alternative embodiments, the gas may be a carrier gas carrying a deposition material for depositing material onto the substrate, or the gas may carry or be a growth enhancer or nutrient source. Other types of carrier gas may be used, and other fluids may be used too such as liquid chemicals that will perform the etch process, usually without the need of a plasma field as the etching that takes place is a chemical process driven by the liquid etchant as opposed to ionized gas.

Figure 6:
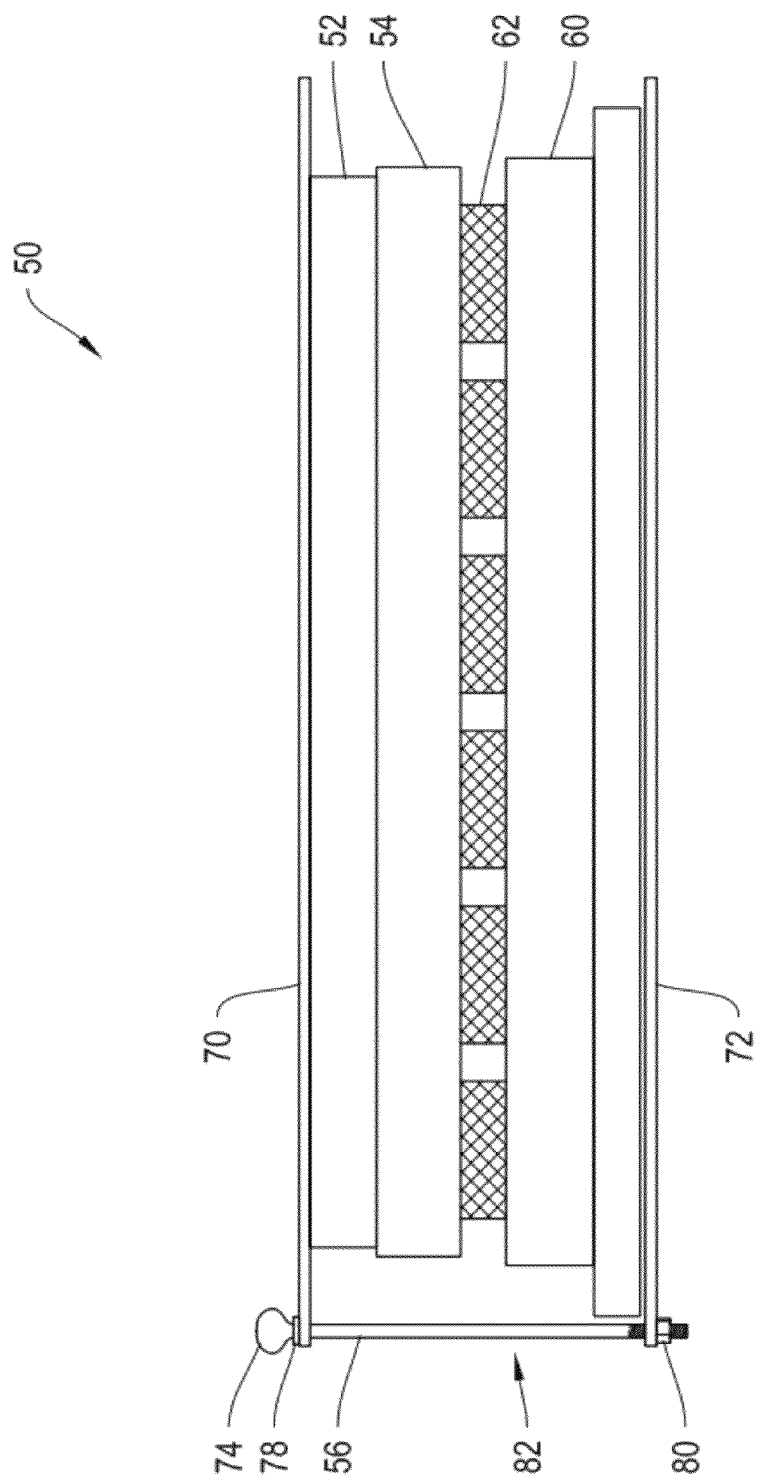
FIG. 6 depicts a side view of the micro-contact stamp of FIG. 1 fitted within a twenty-four well microtiter plate.

Turning to FIG. 6, the microcontacting stamp described above is depicted fitted within a microtiter plate to form the depicted microcontact printing assembly 50. Specifically, FIG. 6 depicts the foam pad 52, guide plate 54, microtiter plate 60 and posts 62. The pad 52, plate 54 and posts 62 are part of the microcontacting stamp 56 that is removably and replaceably positioned within the microtiter plate 60. The assembly 50 is sandwiched between two clamping plates 70 and 72. The clamping plates 70 and 72 are typically flat clear acrylic plates that fully cover the top and bottom of the assembly 50. The plates 70 and 72 are rectangular and at each corner there are slots for a compression bolt. FIG. 6 depicts a side view of one such compression bolt 82, with the other bolts not shown for purpose of clarity.

The compression bolt 82 passes through slots (not shown) in both plates 70 and 72, with a thrust washer 78 on the top plate 70 and a nut 80 under the bottom plate 72. The depicted bolt 87 has a thumb-head that allows the bolt 82 to be readily finger tightened, thus compressing the assembly 50 between the two plates 70 and 72 and generating a force that presses the posts 12 and resilient pads 18 against the bottom surface of respective wells of the microtiter plate 60. Other clamping or pressing devices may be used to drive the stamp 52 into the microtiter plate 60 and the clamp plates 70 and 72 depicted in FIG. 6 are merely illustrative of the type of systems and devices that may be employed.

Figure 7:
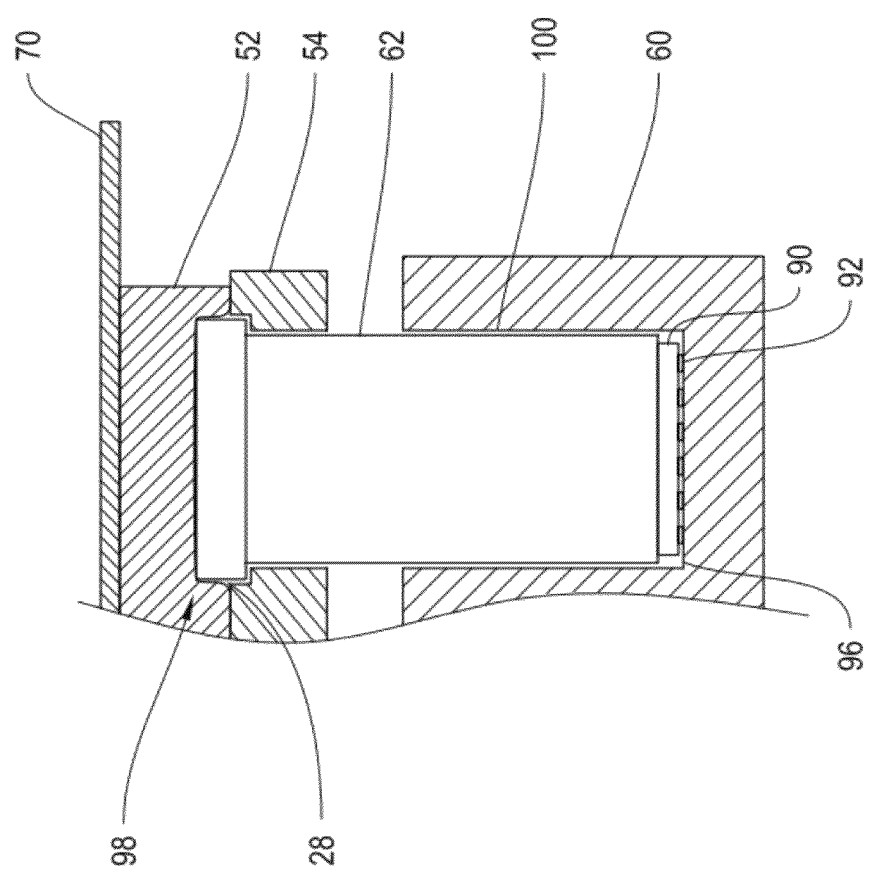
FIG. 7 depicts a side view cutaway of a micro-contact stamp being pressed against the surface of the microtiter plate.

FIG. 7 depicts a cross-sectional view of one post 62 being pressed against the bottom substrate wall 96 of a microtiter plate 60. Specifically, FIG. 7 depicts a post 62 within a well 100 of a microtiter plate 60. The post 62 floats within the aperture 28 of the guide plate 54 such that the post 62 is capable of moving upward toward the compression plate 70 when the post 62 is pressed against the bottom substrate wall 96. As further depicted in FIG. 7 the resilient pad 90 includes a plurality of flat pads 92 that form a pattern on the pad 90 and similarly contact the bottom wall 96, covering a similar pattern on the substrate bottom wall 96. As illustrated, the post 62 may move upwardly through aperture 28 such that the top of the post 62 pushes against and compresses the resilient pad 52. This is depicted in FIG. 7 by the exaggerated compression 98 of the pad 52. In typical practice the pad 52 compresses by amounts essentially smaller that the human eye can detect. The pads 92 are to be brought into select contact with the bottom wall 96. In a typical embodiment, the bottom surface 96 of each well 100 is within one to two thousandths of an inch of each other. Similarly, the tolerance for each post 62 as well as the resilient pad 90 and bottom pads 92 is also about one thousandths of an inch. Thus, the distance from the guide plate 54 to the different bottom surfaces 92 of the wells of plate 60 may vary on the order of one to three thousandths of an inch, and consequently, each respective post 62 may compress the pad 52 by a similar amount.

Figure 8A:
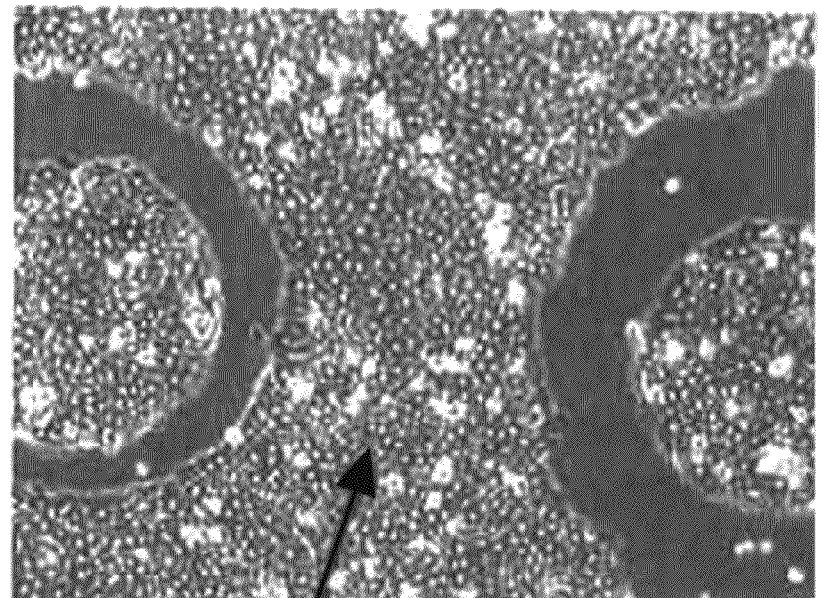
FIG. 8 depict cell islands surrounded by etched substrate areas.
Figure 8B:
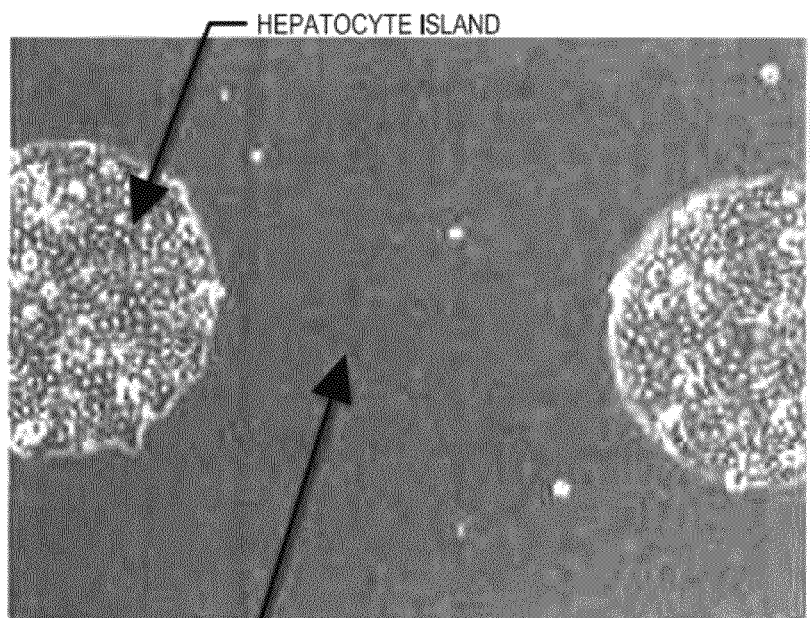

FIGS. 8A and 8B depict a poorly formed cell island and a properly formed cell island respectively. In FIG. 8A the cell island is surrounded by a ring of etched and clean substrate which, in turn, is surrounded by a field of cell material. In contrast, FIG. 8B shows a cell island that is surrounded by a field of etched clean surface. In FIG. 8A, the field of cell material exiting between the cell islands indicates that the resilient pad 90 contacted the substrate surface or otherwise protected that surface from the etching gas. In either case, the result is that the etch gas failed to clear the cell material from between the cell islands. Although not to be bound by theory, it is understood that the failure to etch illustrated in FIG. 8A arises from the over compression of the pads 92 and 90 due to the post 62 being pressed into the well 100, a distance that was between one and three thousandths of an inch too far. This excessive extension compressed the elastomeric pads, deforming them and causing the deformed pad to contact and cover the substrate during the etch process. As the precision required to properly contact the paid 92 against the surface 96 is within the range of a few thousandths of an inch, the floating post 62 held in place by resilient member 54 provides a spring force or load deflection characteristic that allows the post 62 to drive into the pad 54 a distance of several thousandths of an inch before the deflection load force exceeds the deformation force characteristic of the pads 90 and 92. That is, the load deflection force of the resilient pad 54 is selected to be less than the force required to deform the elastomeric pads 90 and 92 an amount sufficient to cause the deformed pads 90 and 92 to improperly contact, either to little or too much, the substrate surface 96.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as broadly as allowed under the law.

I claim:

1. A device for forming patterns of cells on a surface of a substrate, comprising a guide plate having an upper surface and a lower surface and a plurality of apertures extending there through and arranged to align with locations on the surface of the substrate, a plurality of posts each fitted within a respective aperture, a plurality of pads formed of a resilient material and having a pattern of raised plateaus for butting against the surface of the substrate, each of the plurality of pads being fixed to a distal surface of a respective post, and a resilient deformable linkage connecting the posts within the guide plate.

2. The device of claim 1, further comprising
a clamp plate disposed above the guide plate upper surface for applying a mechanical load across the upper surface of the guide plate.

3. The device of claim 1, further comprising
a clamp for forcing the clamp plate against the guide plate with a force selected to seal the pads against the surface of substrate.

4. The device of claim 1, wherein the resilient deformable linkage includes a section of resiliently deformable material.

5. The device of claim 1, wherein the resilient deformable linkage comprises a foam pad adhered to the upper surface of the guide plate.

6. The device of claim 5, wherein an indentation load deflection (ILD) of the first five thousand of an inch of the foam pad is less than the force required to deform the pattern of the pads on the distal end of the posts.

7. The device of claim 1, wherein the pad includes a resilient mask for butting against a biological material on surface of the substrate.

8. The device of claim 1, wherein the pad includes a print pad for delivering a biological material to the surface of the substrate.

9. The device of claim 1, wherein the guide plate includes gas channels in fluid communication with the apertures for delivering plasma gas into the apertures.

10. The device of claim 1, wherein the guide plate apertures are arranged to dispose the plurality of posts in alignment with the wells of a multi-well microtiter plate.

11. The device of claim 1, wherein the posts comprise rigid acrylic posts and the pads comprise PDMS.

12. The device of claim 1, wherein the posts have a retaining member for preventing the posts from passing through the apertures.

13. A manufacturing method for making a patterning mask of the type that forms a pattern of cells onto a surface,
   providing a mask having a desired pattern and made of a material having some resilience to a mechanical force,
   attaching the mask to a projecting post at one end of the projecting post,
   inserting the post within a guide plate such that the post is movably disposed within the guide plate to allow linear movement of the post, and
   providing a compressible layer over the guide plate and into contact with the projecting post, such that the projecting post is held within the guide by the compressible layer.

14. The manufacturing method of claim 13, further including selecting a compressible layer having an indentation load deflection (ILD) selected to resiliently yield at a force less than the force required to deform the mask.

15. The manufacturing method of claim 13, further including forming a plurality of gas channels in fluid communication with the apertures for delivering plasma gas into the apertures.

16. The manufacturing method of claim 13, further including forming the posts as rigid cylindrical members having a diameter selected to fit within a well of a microtiter plate.

17. A method for forming patterns of cells within the wells of a microtiter plate,
   providing a microcontacting stamp having
      a guide plate with an upper surface and a lower surface and a plurality of apertures extending therethrough and arranged to align with the wells of the microtiter plate,
      a plurality of posts fitted within respective apertures and having resilient pads on their distal ends, the pads having raised plateaus for forming the pattern of cells, and
      a resilient deformable linkage connecting the posts within the guide plate, fitting the microcontacting stamp within the microtiter well, and
   applying a clamping force to drive the microcontacting stamp against the microtiter plate to press the pads against the bottom surface of the wells of the microtiter plates.

18. The method of claim 17, further comprising
applying cells to the resilient pads and pressing the pads against the bottom surface of the wells to print the cells on to the surface of the well.

19. The method of claim 17, further comprising
applying a cell adhering material to the bottom surface of the microtiter wells.

20. The method of claim 19, further comprising
forming in the guide plate gas channels in fluid communication with the apertures, and
delivering plasma gas through the gas channels and into the apertures, to etch the cell adhering material from the surface of the microtiter well.

* * * * *